United States Patent [19]

Connor et al.

[11] 4,066,655

[45] Jan. 3, 1978

[54] 4,10-DIHYDRO-4,10-DIOXO-1H-1-BENZOPYRANO[3,2-B]PYRIDINE-3-CARBOXYLIC ACIDS, SALTS AND ESTERS

[75] Inventors: David T. Connor, Parsippany; Patricia A. Young, Madison; Max von Strandtmann, Rockaway, all of N.J.

[73] Assignee: Warner-Lambert Company, Morris Plains, N.J.

[21] Appl. No.: 736,926

[22] Filed: Oct. 29, 1976

[51] Int. Cl.² .............................................. C07D 491/04
[52] U.S. Cl. .......................... 260/295.5 T; 260/295 T; 260/345.2; 424/256
[58] Field of Search ...................... 260/295.5 T, 295 T

[56] References Cited

U.S. PATENT DOCUMENTS

| | | | |
|---|---|---|---|
| 3,632,595 | 1/1972 | Pars et al. | 260/295 T |
| 3,878,219 | 4/1975 | Lee | 260/295 T |
| 3,991,194 | 11/1976 | Harris et al. | 260/295 T |

*Primary Examiner*—Alan L. Rotman

*Attorney, Agent, or Firm*—Albert H. Graddis; Frank S. Chow

[57] ABSTRACT

The present invention relates to 4,10-dihydro-4,10-dioxo-1H-1-benzopyrano[3,2-b]pyridine-3-carboxylic acids, salts and esters having the formula:

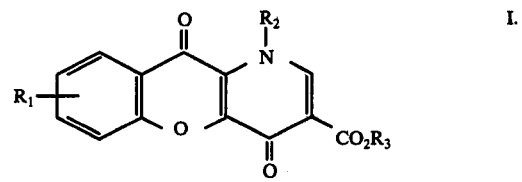

wherein $R_1$ is hydrogen, lower alkyl, halogen, hydroxy or lower alkoxy; $R_2$ is hydrogen, aralkyl or lower alkyl; $R_3$ is hydrogen or lower alkyl and their pharmaceutically acceptable salts.

These compounds are indicated in the management of allergic conditions such as bronchial asthma, hay fever and the like.

15 Claims, No Drawings

4,10-DIHYDRO-4,10-DIOXO-1H-1-BENZOPYRANO[3,2-B]PYRIDINE-3-CARBOXYLIC ACIDS, SALTS AND ESTERS

The present invention relates to 4,10-dihydro-4,10-dioxo-1H-1-benzopyrano[3,2-b]pyridine-3-carboxylic acids, salts and esters having the formula:

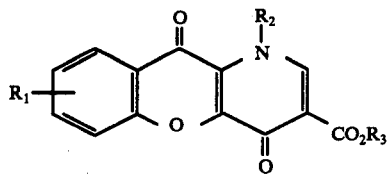

wherein $R_1$ is hydrogen, lower alkyl, halogen, hydroxy or lower alkoxy; $R_2$ is hydrogen, aralkyl or lower alkyl; $R_3$ is hydrogen or lower alkyl and their pharmaceutically acceptable salts.

In the above definitions for $R_1$, $R_2$ and $R_3$, lower alkyl and the lower alkyl portion of lower alkoxy and aralkyl is meant to have 1–6 carbon atoms such as, for example, methyl, ethyl, propyl, isopropyl, butyl, isobutyl, and so on. The aryl portion of aralkyl is meant to be an aromatic hydrocarbon radical, typically of 6–10 carbon atoms such as phenyl, tolyl and so on.

The compounds of the present invention, including their salts, have been found to inhibit and prevent allergic and asthmatic reactions. For example, at a dose of 0.5 to 100 mg/kg intravenously, Compounds I or their salts were found to prevent allergic and asthmatic reactions in the passive cutaneous anaphylaxis (PCA) screen. This PCA screen is a modification of procedures described by I. Mota, *Life Sciences*, 7: 465 (1963) and Z. Ovary and O. Bier, *Proc. Soc. Exptl. Biol. Med.*, 81: 585 (1952). The compound 8-chloro-4,10-dihydro-4,10-dioxo-1H-1-benzopyrano[3,2-b]pyridine-3-carboxylic acid is particularly preferred because at a dose of 0.5 mg/kg, the PCA screen shows a 46% inhibition of the allergic reactions.

In view of the above biological activity, the compounds of this invention, including their salts, are indicated in the management of patients with allergic manifestations such as bronchial asthma and hay fever. Generally speaking, a dose of 0.5 mg/kg to 100 mg/kg orally, parenterally or by inhalation one to three times daily is suggested. As with any anti-allergic therapy, the dosage regimen must be titrated to individual needs by methods well-known to the healing arts.

In order to use these compounds and their salts, they are to be formulated into conventional dosage forms such as tablets, elixers and aerosols by known pharmaceutical technology. For example, tablets can be prepared by selecting the active ingredient, mixing with lactose and compressed into tablets with suitable tabletting excipients known in the art.

The above Compound I is prepared in accordance with the following reaction scheme:

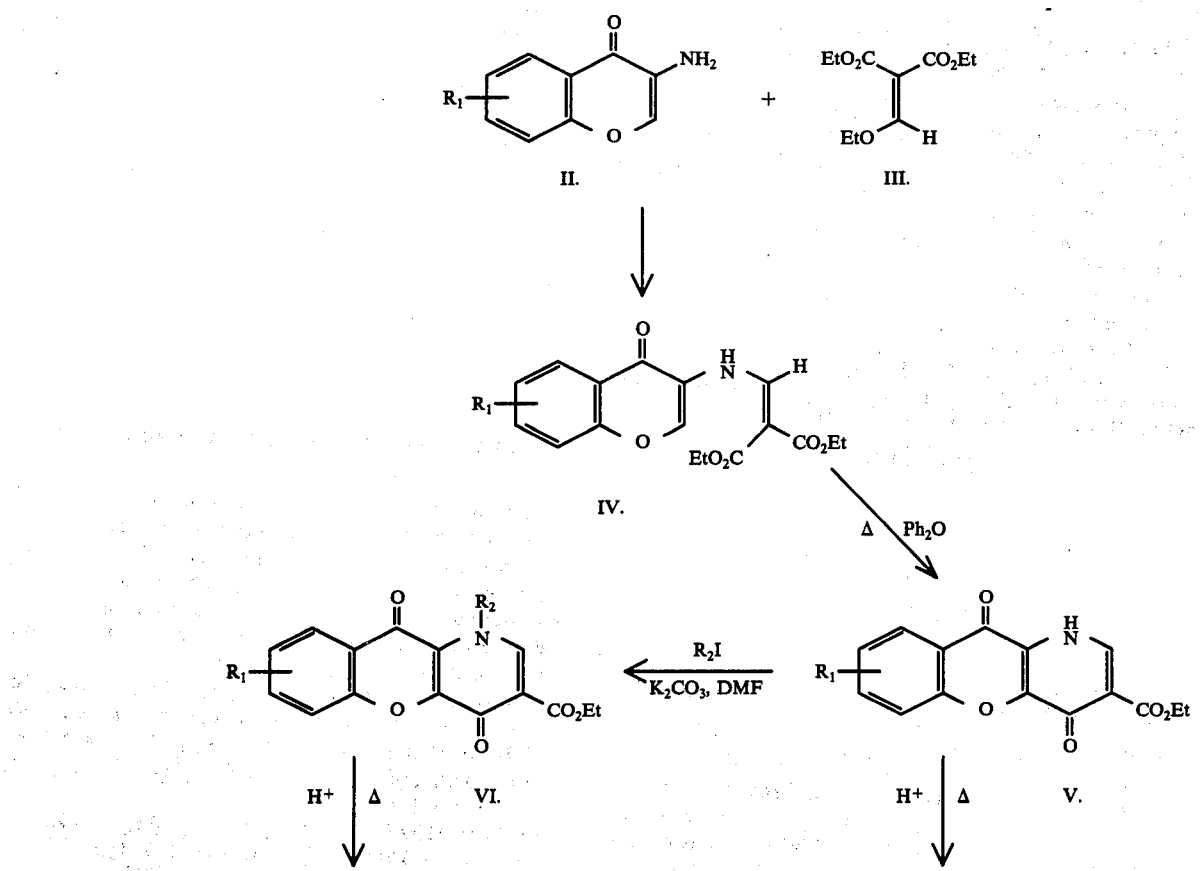

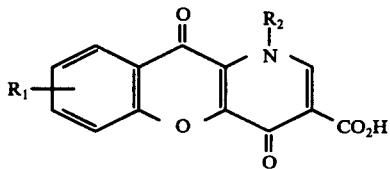

VII.

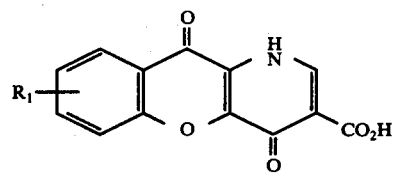

VIII.

Referring to the above reaction scheme, Compound II is treated with Compound III at an elevated temperature, such as about 120° C., under an atmosphere of nitrogen. Compound IV is then treated with diphenyl ether which results in the production of Compound V. In turn, Compound V is treated with $R_2$ iodide in the presence of potassium carbonate and dimethyl formamide under an atmosphere of nitrogen to yield Compound VI. Hydrolysis of Compound VI results in those compounds of the invention in which $R_2$ is other than hydrogen.

Similarly, hydrolysis of Compound V leads directly to those compounds of the invention in which $R_2$ and $R_3$ are hydrogen.

Salts of the carboxylic acids of the present invention are produced by treating the acid with bases such as sodium carbonate, potassium carbonate, calcium carbonate and so on, and recovering the salt by conventional procedures.

Salts of the basic compounds of this invention are prepared by treating the parent base with an acid, for example a mineral acid, such as hydrochloric, sulfuric, nitric and phosphoric in stoichiometric amounts and recovering the salts produced by conventional procedures.

The starting materials were prepared as follows:

3-Aminochromone by the method of G. J. P. Beckett and G. P. Ellis, *Tetrahedron Letters*, 719 (1976); 3-nitro-7-methoxy-4H-1-benzopyran-4-one by the method described in our copending application Ser. No. 710,996 filed Aug. 2, 1976; 3-nitro-6-chloro-4H-1-benzopyran-4-one by the method of M. von Strandtmann and S. Klutchko, U.S. Pat. No. 3,906,005. Diethyl ethoxymethylenemalonate is available from Aldrich Chemical Company.

The aforesaid disclosures are incorporated by reference herein.

To further illustrate the practice of this invention, the following examples are included. The temperatures hereinafter are in degrees Centigrade.

EXAMPLE 1

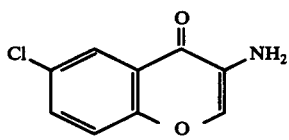

3-Amino-6-chloro-4H-1-benzopyran-4-one

Sodium dithionite (20 g, 0.115 mole) was added to a suspension of 3-nitro-6-chloro-4H-1-benzopyran-4-one (7.0 g, 0.037 mole) in water (80 ml) and absolute ethanol (30 ml). The reaction mixture was refluxed under nitrogen for 3 hrs., concentrated at reduced pressure and filtered. The solids were washed with water and recrystallized from acetone to give yellow crystals (5.44 g, 90%), m.p. 184°–186°.

Anal. Calcd. for $C_9H_6ClNO_2$: C, 55.10; H, 3.06; N, 7.15; Cl, 18.10. Found: C, 55.01; H, 3.14; N, 6.62; Cl, 18.11.

EXAMPLE 2

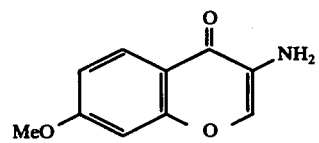

3-Amino-7-methoxy-4H-1-benzopyran-4-one

Sodium dithionite (140 g, 0.804 mole) was added to a suspension of 3-nitro-7-methoxy-4H-1-benzopyran-4-one (50 g, 0.261 mole) in water (330 ml) and absolute ethanol (110 ml). The reaction mixture was stirred for 15 min., concentrated at reduced pressure and filtered. The solids were washed with water and recrystallized from ethyl acetate to give light brown crystals, 159°–162°.

Mass Spectrum: Observed molecular ion, 191.0645; Calculated for $C_{10}H_9NO_3$, 191.0582.

EXAMPLE 3

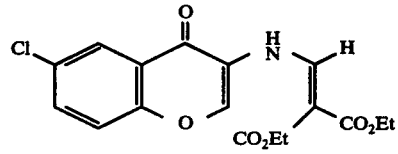

Diethyl {[(6-chloro-4-oxo-4H-1-benzopyran-3-yl)amino]methylene}propanedioate

A mixture of 3-amino-6-chlorochromone (1.95 g, 0.01 mole) and diethyl ethoxymethylenemalonate (3.5 g, 0.016 mole) was heated under nitrogen at 120° for 4 hrs. The reaction mixture was cooled. The product, which precipitated, was filtered off and washed with ethyl acetate. Recrystallization from ethyl acetate gave white crystals (2.51 g, 68%), m.p. 143°–145°.

Anal. Calcd. for $C_{17}H_{16}ClNO_6$: C, 55.82; H, 4.41; N, 3.83; Cl, 9.69. Found: C, 55.86; H, 4.50; N, 3.88; Cl, 9.60.

NMR ($CDCL_3$) δ 10.70 (d, 1, N-H (J = 14Hz) exchanges with $D_2O$), 8.5–7.4 (m, 4, ArH), 4.7–4.0 (m, 4, $CH_2$) and 1.6–1.2 (m, 6, $CH_3$).

IR 3300–3200 (N-H), 1680 (CO) and 1650 (CO).

UV 217 (23,000), 292 (23,000), 323 (26,000).

EXAMPLE 4

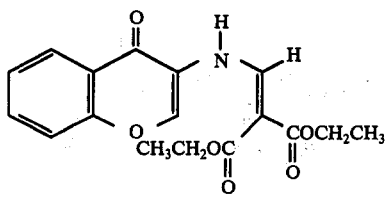

Diethyl {[(4-oxo-4H-1-benzopyran-3-yl)amino]methylene}propanedioate

A mixture of 3-aminochromone (8.0 g, 0.05 mole) and diethyl ethoxymethylenemalonate (17.3 g, 0.08 mole) was heated under nitrogen at 140° C. for 2.5 hrs. The reaction mixture was cooled. The product, which crystallized out was filtered off and triturated with petroleum ether. Recrystallization from ethyl acetate - absolute ethanol gave white crystals (10.3 g, 62.5%), m.p. 155°–157° C.

Anal. Calcd. for $C_{17}H_{17}NO_6$: C, 61.63; H, 5.17; N, 4.23. Found: C, 61.64; H, 5.27; N, 4.43.

NMR (CDCl$_3$) δ 10.70 (d, 1, NH, J = 14 Hz, exchanges with D$_2$O), 8.30 (d, 1, CH, J = 14Hz, collapses to singlet with D$_2$O), 8.11 (s, 1, C$_2$H), 7.55 (m, 4, ArH), 4.35 (q, 2, CH$_2$, J = 7Hz), 4.28 (q, 2, CH$_2$, J = 7Hz), 1.49 (t, 3, CH$_3$, J = 7Hz), 1.32 (t, 3, CH$_3$, J = 7Hz).

IR 3095 (NH), 1675 (CO), 1642 (CO).

UV 218 (23,000), 284 (20,400), 320 (28,000).

EXAMPLE 5

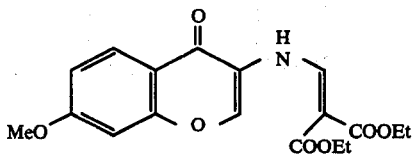

Diethyl {[(7-methoxy-4-oxo-4H-1-benzopyran-3-yl)amino]methylene}propanedioate.

Prepared by the procedure described for Example 4 from crude 3-amino-7-methoxy-4-H-1-benzopyran-4-one (35 g). Recrystallization from ethyl acetate gave pale yellow crystals (22.5 g, 34%), m.p. 139°–141° C.

Anal. Calcd. for $C_{18}H_{19}NO_7$: C, 59.83; H, 5.30; N, 3.88. Found: C, 59.81; H, 5.15; N, 3.75.

NMR (CDCl$_3$) δ 10.70 (d, 1, NH, exchanges with D$_2$O, J = 14Hz), 8.30 (d, 1, CH, collapses to singlet with D$_2$O, J = 14Hz), 8.03 (s, 1, C$_2$H), 8.19 (d, 1, C$_5$H), 7.0 (m, 2, C$_6$H and C$_8$H), 4.32 (m, 4, 2CH$_2$), 3.95 (s, 3, OCH$_3$) and 1.40 (m, 6, 2CH$_3$).

IR 3100 (NH), 1685 (CO), 1652 (CO), 1620 (CO).

UV 230 (20,500), 299 (32,450).

EXAMPLE 6

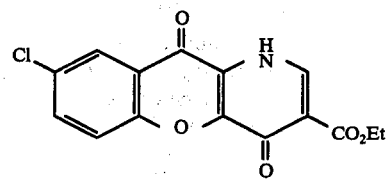

Ethyl 8-chloro-4,10-dihydro-4,10-dioxo-1H-1-benzopyrano[3,2-b]pyridine-3-carboxylate Diethyl {[(6-chloro-4-oxo-4H-1-benzopyran-3-yl)amino]methylene}propanedioate (5.0 g, 0.0137 mole) was added to diphenyl ether (30 ml) at 200°. The reaction mixture was refluxed (bath temp. 280°–290°) for 60 min. The product, which crystallized out on cooling, was filtered off and washed with ether. Recrystallization from DMF gave white crystals (4.05 g, 93%), m.p. 330°–338° (dec).

Anal. Calcd. for $C_{15}H_{10}ClNO_5$: C, 56.35; H, 3.15; N, 4.38; Cl, 11.09. Found: C, 56.35; H, 3.23; N, 4.34; Cl, 11.17.

NMR (TFA) δ 9.41 (s, 1, C$_2$H), 8.50 to 7.90 (m, 3, ArH), 4.78 (q, 2, CH$_2$), 1.61 (t, 3, CH$_3$).

IR 3300–3000 (NH), 1730 (CO), 1680 (CO).

UV 247 (24,000), 262 (27,000), 354 (7,200).

EXAMPLE 7

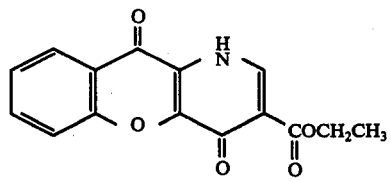

Ethyl 4,10-dihydro-4,10-dioxo-1H-1-benzopyrano[3,2-b]pyridine-3-carboxylate

Prepared by the method described for Example 6 from diethyl {[(4-oxo-4H-1-benzopyran-3-yl)amino]methylene}propanediaote (3.18 g, 0.096 mole). Recrystallization from DMF gave off-white crystals (1.65 g, 52%), m.p. 294°–295° C.

Anal. Calcd. for $C_{15}H_{11}NO_5$: C, 63.16; H, 3.89; N, 4.91. Found: C, 63.09; H, 3.91; N, 4.94.

NMR (TFA) δ 9.41 (s, 1, C$_2$H), 8.52 (m.d., 1, ArH), 8.02 (m, 3ArH), 4.80 (q, 2, CH$_2$, J = 7Hz), 1.62 (t, 3, CH$_3$, J = 7Hz).

IR 3160 (NH), 3080 (NH), 1730 (CO), 1675 (CO), 1632 (CO).

UV 242 (22,100), 257 (22,400), 347 (7,400).

EXAMPLE 8

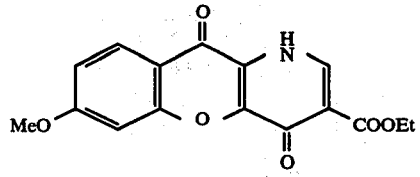

Ethyl 7-methoxy-4,10-dihydro-4,10-dioxo-1H-1-benzopyrano[3,2b-]pyridine-3-carboxylate Prepared by the method described for Example 6 from diethyl {[(7-methoxy-4-oxo-4H-1-benzopyran-3-yl)amino]methylene}propanedioate (20.0 g, 0.0555 mole). Recrystallization from DMF gave white crystals (11.3 g, 64.5%), m.p. 277°–280° C.

Anal. Calcd. for $C_{16}H_{13}NO_6$: C, 60.95; H, 4.16; N, 4.44. Found: C, 60.80; H, 4.34; N, 4.68.

EXAMPLE 9

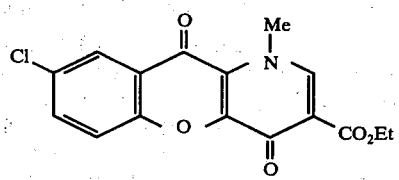

Ethyl 1-methyl-8-chloro-4,10-dihydro-4,10-dioxo-1H-1-benzopyrano[3,2-b]pyridine-3-carboxylate A mixture of ethyl 8-chloro-4,10-dihydro-4,10-dioxo-1H-1-benzopyrano[3,2-b]pyridine-3-carboxylate (0.5 g, 0.0016 mole), methyl iodide (0.5 g, 0.0035 mole) and potassium carbonate (0.23 g, 0.0017 mole) in dimethyl formamide (25 ml) was stirred at 100° for 3 hrs. under nitrogen. The reaction mixture was cooled. The product, which precipitated, was filtered, washed with water and dried. Recrystallization from DMF gave white crystals (0.47 g, 90%), m.p. 295°–297°.

Anal. Calcd. for $C_{16}H_{12}ClNO_5$: C, 57.59; H, 3.62; N, 4.20; Cl, 10.62. Found: C, 57.43; H, 3.68; N, 4.15; Cl, 10.69.

NMR (TFA) δ 9.25 (s, 1, $C_2H$), 8.60 to 7.80 (m, 3, ArH), 4.92 (s, 3, $CH_3N$), 4.80 (q, 2, $C_2$), 1.62 (t, 3, $CH_3$).

IR 1685 (CO), 1645 (CO).

UV 240 (24,000), 252 (26,000), 264 (24,000), 295 (9,500), 345 (8,500), 356 (8,500).

EXAMPLE 10

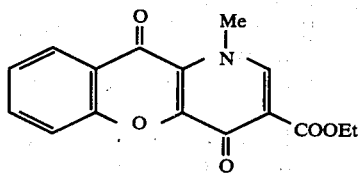

Ethyl 1-methyl-4,10-dihydro-4,10-dioxo-1H-1-benzopyrano[3,2-b]pyridine-3-carboxylate Prepared by the method described for Example 9 from ethyl 4,10-dihydro-4,10-dioxo-1H-1-benzopyrano[3,2-b]pyridine-3-carboxylate (8.0 g, 0.028 mole). Recrystallization from DMF gave off-white crystals (8.25 g, 98.5%), m.p. 251°–254° C.

Anal. Calcd. for $C_{16}H_{13}NO_5$: C, 64.21; H, 4.38; N, 4.68. Found: C, 64.22; H, 4.39; N, 4.69.

NMR (TFA) δ 9.28 (s, 1, $C_2H$), 8.53 & 8.01 (d & m, 4, ArH), 4.99 (s, 3, $CH_3N$), 4.83 (q, 2, $CH_2$, J = 7Hz), 1.68 (t, 3, $CH_3$, J = 7Hz).

IR 1683 (CO), 1645 (CO).

UV 247 (24,100), 338 (8,500).

EXAMPLE 11

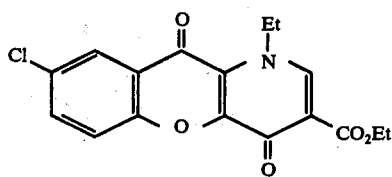

Ethyl 1-ethyl-8-chloro-4,10-dihydro-4,10-dioxo-1H-1-benzopyrano[3,2-b]pyridine-3-carboxylate Prepared from ethyl 8-chloro-4,10-dihydro-4,10-dioxo-1H-1-benzopyrano[3,2-b]pyridine-3-carboxylate (3.19 g, 0.01 mole) and ethyl iodide (6.24 g, 0.04 mole) by the method described for Example 9. Recrystallization from DMF gave white crystals (2.7 g, 78%), m.p. 257°–259°.

Anal. Calcd. for $C_{17}H_{14}ClNO_5$: C, 58.72; H, 4.06; N, 4.03; Cl, 10.20. Found: C, 58.56; H, 4.01; N, 4.07; Cl, 10.26.

NMR (TFA) δ 9.28 (s, 1, $C_2H$), 8.60 to 7.80 (m, 3, ArH), 5.45 (q, 2, $CH_2$—N), 4.83 (q, 2, $CH_2$—O), 1.82 (t, 3, $CH_3$) and 1.68 (t, 3, $CH_3$).

IR 1685 (CO), 1650 (CO).

UV 240 (24,000), 252 (27,000), 263 (25,000), 295 (9,500), 347 (9,000), 363 (9,000).

EXAMPLE 12

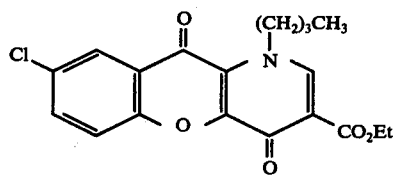

Ethyl 1-butyl-8-chloro-4,10-dihydro-4,10-dioxo-1H-1-benzopyrano [3,2-b]pyridine-3-carboxylate Prepared from ethyl 8-chloro-4,10-dihydro-4,10-dioxo-1H-1-benzopyrano[3,2-b]pyridine-3-carboxylate (3.195 g, 0.01 mole) and butyl iodide (7.36 g, 0.04 mole) by the method described for Example 9. Recrystallization from methanol gave white crystals (3.575 g, 95%), m.p. 226°–228°.

Anal. Calcd. for $C_{19}H_{18}ClNO_5$: C, 60.73; H, 4.83; N, 3.73; Cl, 9.43. Found: C, 60.74; H, 4.68; N, 3.72; Cl, 9.60.

NMR (TFA) δ 9.28 (s, 1, $C_2H$), 8.60 to 7.80 (m, 3ArH), 5.40 (t, 2, $CH_2$—N), 4.85 (q, 2, $CH_2$—O) and 2.50 to 1.00 (m, 10 aliphatic).

IR 1685 (CO), 1645 (CO).

UV 240 (24,000), 252 (27,000), 263 (25,000), 295 (9,500), 347 (9,000), 363 (9,000).

EXAMPLE 13

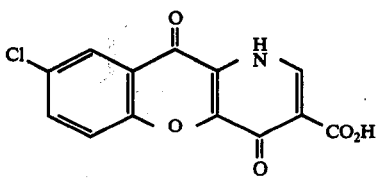

8-Chloro-4,10-dihydro-4,10-dioxo-1H-1-benzopyrano[3,2-b]pyridine-3-carboxylic acid A suspension of ethyl 8-chloro-4,10-dihydro-4,10-dioxo-1H-1-benzopyrano[3,2-b]pyridine-3-carboxylate (3.0 g, 0.0094 mole) in 6N hydrochloric acid (100 ml) was refluxed under nitrogen for 15 hrs., cooled and filtered. The residue was washed with water and with acetone. Recrystallization from DMF gave white crystals (2.4 g, 87%), m.p. 325°–327°.

Anal. Calcd. for $C_{13}H_6NO_5Cl$: C, 53.54; H, 2.07; N, 4.80; Cl, 12.16. Found: C, 53.25; H, 2.18; N, 4.81; Cl, 12.29.

NMR (TFA) δ 9.33 (s, 1, $C_2H$), 8.60 to 7.60 (m, 3, ArH).

IR 3250 (NH), 2800–2500 (OH), 1745 (CO), 1675 (CO), 1630 (CO).

UV 257 (30,000), 352 (7,200).

EXAMPLE 14

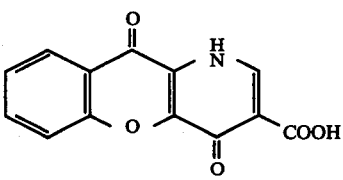

4,10-Dihydro-4,10-dioxo-1H-1-benzopyrano[3,2-b]pyridine-3-carboxylic acid

Prepared by the method described for Example 13 from ethyl 4,10-dihydro-4,10-dioxo-1H-1-benzopyrano[3,2-b]pyridine-3-carboxylate (5.0 g, 0.0175 mole). Recrystallization from DMF gave white crsytals (4.13 g, 94%), m.p. dec > 330° C.

Anal. Calcd. for $C_{13}H_7NO_5$: C, 60.71; H, 2.74; N, 5.45. Found: C, 60.61; H, 2.94; N, 5.73.

NMR (TFA) δ 9.35 (s, 1, $C_2H$), 8.7–7.6 (m, 4, ArH).

IR 3180 (NH), 3050 (C<u>OO</u>H), 2800–2300 (COO<u>H</u>), 1730 (CO), 1670 (CO), 1625 (CO).

UV 244 (shoulder) (24,400), 252 (27,160), 336 (shoulder) (6,840), 346 (7,120).

EXAMPLE 15

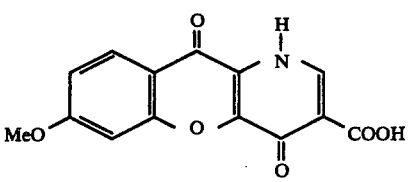

7-Methoxy-4,10-dihydro-4,10-dioxo-1H-1-benzopyrano[3,2-b]pyridine-3-carboxylic acid Prepared by the procedure described for Example 13 from ethyl 7-methoxy-4,10-dihydro-4,10-dioxo-1H-1-benzopyrano[3,2-b]pyridine-3-carboxylate (850 mg). Recrystallization from DMF gave white crystals (640 mg, 82.5%), m.p. 318°–319° C.

Anal. Calcd. for $C_{14}H_9NO_6$: C, 58.54; H, 3.16; N, 4.88. Found: C, 58.35; H, 3.27; N, 4.86.

EXAMPLE 16

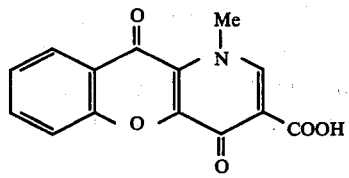

1-Methyl-4,10-dihydro-4,10-dioxo-1H-1-benzopyrano[3,2-b]pyridine-3-carboxylic acid Prepared by the method described for Example 13 from ethyl 1-methyl-4,10-dihydro-4,10-dioxo-1H-1-benzopyrano[3,2-b]pyridine-3-carboxylate (6.0 g, 0.02 mole). Recrystallization from DMF gave pinkish white crystals (4.8 g, 87.5%), m.p. 308°–312°.

Anal. Calcd. for $C_{14}H_9NO_5$: C, 61.99; H, 3.34; N, 5.16. Found: C, 61.84; H, 3.41; N, 5.12.

NMR (TFA) δ 9.19 (s, 1, $C_2H$), 8.48 (d, 1, ArH), 7.96 (m, 3, ArH), 4.92 (s, 3, $CH_3$).

IR 2600 (COOH) broad, 1730 (CO), 1675 (CO), 1629 (CO).

UV 207 (21,000), 251 (27,300), 352 (8,000).

EXAMPLE 17

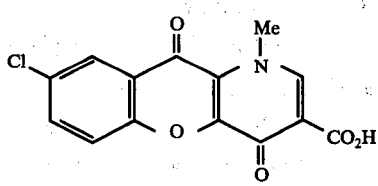

1-Methyl-8-chloro-4,10-dihydro-4,10-dioxo-1H-1-benzopyrano[3,2-b]pyridine-3-carboxylic acid Prepared by the method described for Example 13 from ethyl 1-methyl-8-chloro-4,10-dihydro-4,10-dioxo-1H-1-benzopyrano[3,2-b]pyridine-3carboxylate (3.0 g, 0.009 mole). Recrystallization from DMF gave white crystals (2.35 g, 86%), m.p. 295°–297°.

Anal. Calcd. for $C_{14}H_8ClNO_5$: C, 55.01; H, 2.64; N, 4.58; Cl, 11.60. Found: C, 55.20; H, 2.81; N, 4.64; Cl, 11.62.

NMR (TFA) δ 9.17 (s, 1, $C_2H$), 8.60 to 7.80 (m, 3, ArH), 4.83 (s, 3, $CH_3$).

IR 3070 (OH), 2800–2500 (OH), 1735 (CO), 1665 (CO).

UV 258 (28,500), 342 (8,000), 357 (8,000).

EXAMPLE 18

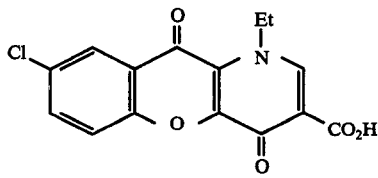

1-Ethyl-8-chloro-4,10-dihydro-4,10-dioxo-1H-1-benzopyrano[3,2-b]pyridine-3-carboxylic acid Prepared by the method described for Example 13 from ethyl 1-ethyl-8-chloro-4,10-dihydro-4,10-dioxo-1H-1-benzopyrano[3,2-b]pyridine-3-carboxylate (3.47 g, 0.01 mole). Recrystallization from DMF gave white crystals (2.97 g, 93%), m.p. 295°°–300° (dec).

Anal. Calcd. for $C_{15}H_{10}ClNO_5$: C, 56.35; H, 3.15; N, 4.38; Cl, 11.09. Found: C, 56.09; H, 3.34; N, 4.71; Cl, 11.07.

NMR (TFA) δ 9.17 (s, 1, $C_2H$), 8.60 to 7.80 (m, 3, ArH), 5.28 (q, 2, $CH_2$) and 1.75 (t, 3, $CH_3$).

IR 3070 (OH), 2800–2500 (OH), 1715 (CO), 1665 (CO).

UV 256 (28,500), 344 (8,000), 356 (8,000).

EXAMPLE 19

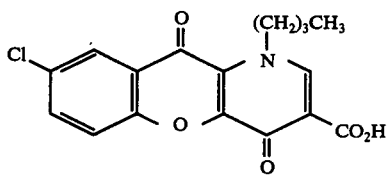

1-Butyl-8-chloro-4,10-dihydro-4,10-dioxo-1H-1-benzopyrano[3,2-b]pyridine-3-carboxylic acid Prepared by the method described for Example 13 from ethyl 1-butyl-8-chloro-4,10-dihydro-4,10-dioxo-1H-1-benzopyrano[3,2-b]pyridine-3-carboxylate (3.40 g, 0.009 mole). Recrystallization from DMF gave white crystals (2.84 g, 90%), m.p. 271°–273°.

Anal. Calcd. for $C_{17}H_{14}ClNO_5$: C, 58.72; H, 4.06; N, 4.03; Cl, 10.20. Found: C, 58.42; H, 4.01; N, 3.81; Cl, 10.35.

NMR (TFA) δ 9.17 (s, 1, $C_2H$), 8.60 to 7.80 (m, 3, ArH), 5.22 (t, 2, $CH_2N$) and 2.50 to 1.00 (m, 7 aliphatic).

IR 3060 (OH), 2800–2500 (OH), 1730 (CO), 1660 (CO).

UV 257 (29,000), 348 (8,000), 358 (8,000).

We claim:

1. A compound of the formula:

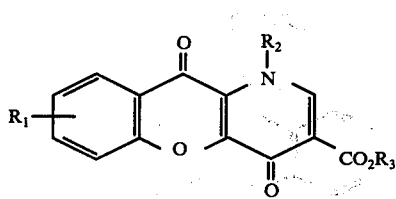

wherein $R_1$ is hydrogen, lower alkyl, halogen, hydroxy or lower alkoxy; $R_2$ is hydrogen phenyl lower alkyl or lower alkyl; $R_3$ is hydrogen or lower alkyl and their pharmaceutically acceptable salts.

2. A compound according to claim 1 which is ethyl 8-chloro-4,10-dihydro-4,10-dioxo-1H-1-benzopyrano[3,2-b]pyridine-3-carboxylate.

3. A compound according to claim 1 which is ethyl 4,10-dihydro-4,10-dioxo-1H-1-benzopyrano[3,2-b]pyridine-3-carboxylate.

4. A compound according to claim 1 which is ethyl 7-methoxy-4,10-dihydro-4.10-dioxo-1H-1-benzopyrano[3,2-b]pyridine-3-carboxylate.

5. A compound according to claim 1 which is ethyl 1-methyl-8-4,10-dihydro-4,10-dioxo-1H-1-benzopyrano[3,2-b]pyridine-3-carboxylate.

6. A compound according to claim 1 which is ethyl 1-methyl-4,10-dihydro-4,10-dioxo-1H-1-benzopyrano[3,2-b]pyridine-3-carboxylate.

7. A compound according to claim 1 which is ethyl 1-ethyl-8-chloro-4,10-dihydro-4,10-dioxo-1H-1-benzopyrano[3,2-b]pyridine-3-carboxylate.

8. A compound according to claim 1 which is ethyl 1-butyl-8-chloro-4,10-dihydro-4,10-dioxo-1H-1-benzopyrano[3,2-b]pyridine-3-carboxylate.

9. A compound according to claim 1 which is 8-chloro-4,10-dihydro-4,10-dioxo-1H-1-benzopyrano[3,2-b]pyridine-3-carboxylic acid.

10. A compound according to claim 1 which is 4,10-dihydro-4,10-dioxo-1H-1-benzopyrano[3,2-b]pyridine-3-carboxylic acid.

11. A compound according to claim 1 which is 7-methoxy-4,10-dihydro-4,10-dioxo-1H-1-benzopyrano[3,2-b]pyridine-3-carboxylic acid.

12. A compound according to claim 1 which is 1-methyl-4,10-dihydro-4,10-dioxo-1H-1-benzopyrano[3,2-b]pyridine-3-carboxylic acid.

13. A compound according to claim 1 which is 1-methyl-8-chloro-4,10-dihydro-4,10-dioxo-1H-1-benzopyrano[3,2-b]pyridine-3-carboxylic acid.

14. A compound according to claim 1 which is 1-ethyl-8-chloro-4,10-dihydro-4,10-dioxo-1H-1-benzopyrano[3,2-b]pyridine-3-carboxylic acid.

15. A compound according to claim 1 which is 1-butyl-8-chloro-4,10-dihydro-4,10-dioxo-1H-1-benzopyrano[3,2-b]pyridine-3-carboxylic acid.

* * * * *